(12) United States Patent
Levin

(10) Patent No.: US 10,426,573 B2
(45) Date of Patent: Oct. 1, 2019

(54) CUSTOMIZED ROOT CANAL OBTURATION CORES AND METHODS OF MAKING CUSTOMIZED ROOT CANAL OBTURATION CORES

(71) Applicant: Martin David Levin, Bethesda, MD (US)

(72) Inventor: Martin David Levin, Bethesda, MD (US)

( * ) Notice: Subject to any disclaimer, the term of this patent is extended or adjusted under 35 U.S.C. 154(b) by 0 days.

(21) Appl. No.: 15/593,095

(22) Filed: May 11, 2017

(65) Prior Publication Data

US 2017/0245961 A1    Aug. 31, 2017

Related U.S. Application Data

(63) Continuation-in-part of application No. 14/460,970, filed on Aug. 15, 2014, now Pat. No. 9,668,824.

(51) Int. Cl.
*A61C 5/04* (2006.01)
*A61C 5/50* (2017.01)
(Continued)

(52) U.S. Cl.
CPC ............ *A61C 5/50* (2017.02); *A61C 13/0004* (2013.01); *A61C 13/0013* (2013.01);
(Continued)

(58) Field of Classification Search
CPC ... A61C 5/04; A61C 13/0019; A61C 13/0004; A61C 9/0053; A61C 13/0013;
(Continued)

(56) References Cited

U.S. PATENT DOCUMENTS

| 4,565,722 A | 1/1986 | Highgate et al. |
| 6,264,471 B1 | 7/2001 | Martin |

(Continued)

FOREIGN PATENT DOCUMENTS

| CN | 101803958 A | 8/2010 |
| CN | 103083094 A | 5/2013 |

(Continued)

OTHER PUBLICATIONS

International Search Report and Written Opinion for International Appl. No. PCT/US2015/044842, European Patent Office, dated Oct. 16, 2015, 14 pages.

(Continued)

*Primary Examiner* — Rex R Holmes
(74) *Attorney, Agent, or Firm* — Sterne, Kessler, Goldstein & Fox P.L.L.C.

(57) ABSTRACT

A core for obturating a root canal includes a body that has a pre-formed contour that closely matches a contour of the root canal. When the core is inserted in the root canal with or without sealer, there are essentially no voids in the root canal. A method of making a customized root canal obturation core includes generating a three-dimensional image of a root canal. The method also includes manufacturing the customized root canal obturation core based on the three-dimensional image of the root canal. The customized root canal obturation core has a preformed contour that closely matches a contour of the root canal such that when the core is inserted in the root canal with or without sealer there are essentially no voids in the root canal.

26 Claims, 16 Drawing Sheets

(51) Int. Cl.
  *A61C 13/00*    (2006.01)
  *G05B 19/4097*  (2006.01)
  *B29C 64/386*   (2017.01)
  *A61B 5/055*    (2006.01)
  *A61B 5/107*    (2006.01)
  *B33Y 80/00*    (2015.01)
  *B33Y 10/00*    (2015.01)
  *B33Y 50/02*    (2015.01)

(52) U.S. Cl.
  CPC ...... *A61C 13/0018* (2013.01); *A61C 13/0019* (2013.01); *B29C 64/386* (2017.08); *G05B 19/4097* (2013.01); *A61B 5/055* (2013.01); *A61B 5/1072* (2013.01); *A61B 2576/02* (2013.01); *A61C 2201/002* (2013.01); *A61C 2201/005* (2013.01); *B33Y 10/00* (2014.12); *B33Y 50/02* (2014.12); *B33Y 80/00* (2014.12)

(58) Field of Classification Search
  CPC ............ A61C 13/0018; B29C 67/0088; G05B 19/4097; A61B 5/055; A61B 6/14; B33Y 50/02; B33Y 10/00; B33Y 80/00
  See application file for complete search history.

(56) References Cited

U.S. PATENT DOCUMENTS

| | | | |
|---|---|---|---|
| 7,210,935 | B2 | 5/2007 | Highgate et al. |
| 9,492,360 | B2* | 11/2016 | Jia ................. A61K 6/0023 |
| 2002/0168615 | A1* | 11/2002 | Kimmel ............ A61C 13/30 433/221 |
| 2004/0248067 | A1 | 12/2004 | Lopez et al. |
| 2004/0265783 | A1 | 12/2004 | Karmaker et al. |
| 2010/0092923 | A1 | 4/2010 | Stites |
| 2012/0065943 | A1* | 3/2012 | Fisker ............ A61C 13/0004 703/1 |
| 2013/0171580 | A1* | 7/2013 | Van Lierde .......... A61B 6/14 433/29 |
| 2013/0209961 | A1 | 8/2013 | Rubbert et al. |
| 2014/0147815 | A1* | 5/2014 | Sicurelli ............ A61C 13/30 433/220 |

FOREIGN PATENT DOCUMENTS

| | | |
|---|---|---|
| WO | WO 2013/181105 A1 | 12/2013 |
| WO | WO 2014/115090 A1 | 7/2014 |
| WO | WO 2016/025587 A1 | 2/2016 |

OTHER PUBLICATIONS

Gutmann et al. "Root Canal Obturation: An Update", Academy of General Dentistry, not dated, pp. 1-11.

Barborka et al., "Long-term Clinical Outcome of Teeth Obturated with Resilon", Journal of Endodontics, vol. 43, Issue 4, Apr. 2017, pp. 556-560.

Cetenovic et al., "Biocompatibility Investigation of New Endodontic Materials Based on Nanosynthesized Calcium Silicates Combined with Different Radiopacifiers", Journal of Endodontics, vol. 43, Issue 3. Mar. 2017. pp. 425-432.

International Search Report and Written Opinion for International Appl. No. PCT/US2018/031142, European Patent Office, dated Oct. 16, 2018, 15 pages.

William Cheung, "A review of the management of endodontically treated teeth: Post, core and the final restoration," Journal of American Dental Association (JADA), vol. 136, May 2005, pp. 611-619.

Vibha Hegde and Shashank Arora, "Sealing ability of a novel hydrophilic vs. conventional hydrophobic obturation systems: A bacterial leakage study," Journal of Conservative Dentistry, vol. 18, Issue 1, Jan.-Feb. 2015, pp. 62-65.

Li et al., "Ability of New Obturation Materials to Improve the Seal of the Root Canal System—A Review," Acta Biomaterialia, vol. 10, Issue 3, Mar. 2014, pp. 1050-1063.

Shweta Tekriwal and Aniket Kumar, "Comparative Evaluation of Volumetric Changes of Propoint Obturating System: An In Vitro Study," Annals of International Medical and Dental Research, vol. 3, Issue 4, May 2017, pp. 9-12.

\* cited by examiner

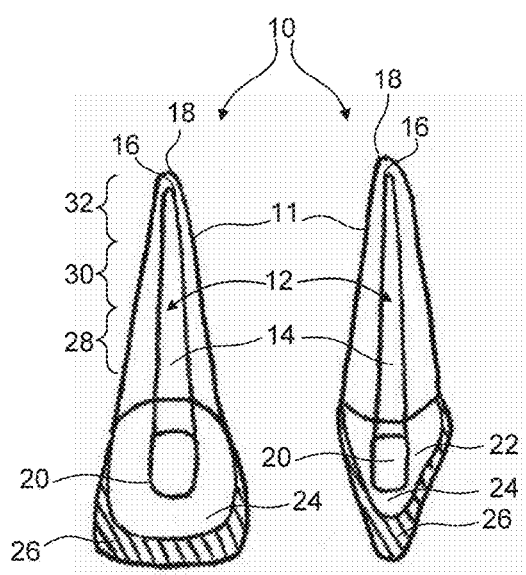 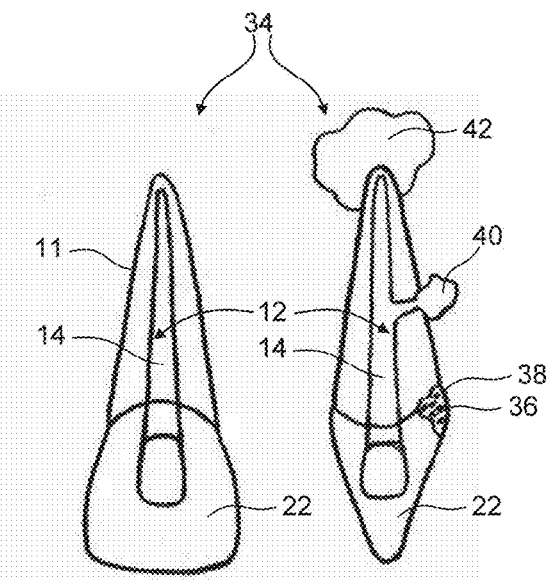
FIG. 1A  FIG. 1B  FIG. 2A  FIG. 2B

| Test | Tooth #8 | Tooth #9 | Tooth #10 |
|---|---|---|---|
| Percussion | Normal | +++ | Normal |
| Palpation | Normal | ++ | Normal |
| Cold | Normal | - | Normal |
| Hot | Normal | +++ lingering | Normal |
| Electric Pulp Test | Normal | No response | Normal |
| Biting | Normal | +++ | Normal |
| Mobility | Normal | + | Normal |
| Discoloration of Crown | Normal | Discolored, gray | Normal |
| Periodontal Findings | Normal | Normal | Normal |

FIG. 5

CUSTOMIZED ROOT CANAL OBTURATION CORES AND METHODS OF MAKING CUSTOMIZED ROOT CANAL OBTURATION CORES

CROSS REFERENCE TO RELATED APPLICATION

This application is a continuation-in-part of U.S. application Ser. No. 14/460,970 (issued as U.S. Pat. No. 9,668,824 on Jun. 6, 2017), filed Aug. 15, 2014, which is hereby incorporated herein in its entirety by reference.

BACKGROUND

Field

Embodiments of the present inventions are generally related to root canal obturation and more specifically to customized root canal obturation cores and methods of and systems for making customized root canal obturation cores.

Background

A tooth includes a root canal that encases a pulp. Bacteria introduced into the pulp can cause inflammation or infection. Once the pulp becomes inflamed or infected, the pulp can be removed to restore the area to health. To prevent bacteria from entering the root canal after removing the pulp, inactivate or entomb remaining bacteria, or seal the root canal from infiltration of external tissue fluids emanating from the tooth-supporting structures, the canal is obturated using a filler material. The filler material typically includes, for example, gutta percha placed incrementally with lateral compaction of individual gutta percha cones, gutta percha placed incrementally with warm vertical compaction, a single gutta percha cone, gutta percha on a carrier of a similar or different core material, a polymeric hydrogel attached to a central nylon core, or a sealer-only material applied to the full length of the canal.

An obturation with voids in the root canal and leakage between the filler material and the root canal increases the risk of re-infection and reduces the chance of long-term success of the root canal procedure. There are typically two kinds of leakage: (1) coronal leakage and (2) lateral canal or apical leakage. Coronal leakage refers to when microorganisms from the oral cavity enter the root canal system via seepage in the restorative seal covering the filler material. Lateral canal or apical leakage occurs when the lateral and apical root segments are infiltrated by peptides and other molecules from the surrounding tissues that support microbial growth in the obturated root canal system. Microbial and tissue fluid infiltration of the root canal system obturated with gutta percha can occur in as little as three weeks. Filler materials used today, except for paste-only obturation techniques, typically consist of using a solid core material placed with a paste or sealer component. These techniques can generate significant voids in the root canal, which can lead to leakage, infection, and eventual re-treatment or tooth loss. And it is difficult to entirely fill ribbon-shaped and widely oval-shaped canals. According, there is a need for an obturation system that substantially fills the entire root canal without voids for variously shaped root canals.

BRIEF SUMMARY

In some embodiments, a core for obturating a root canal includes a body that has a pre-formed contour that closely matches a contour of the prepared and disinfected root canal. When the core is inserted in the root canal, there are essentially no voids in the root canal.

In some embodiments, a method of making a customized root canal obturation core includes generating a three-dimensional image of a root canal. The method also includes manufacturing the customized root canal obturation core based on the three-dimensional image of the root canal. The customized root canal obturation core has a contour that closely matches a contour of the root canal such that when the core is inserted in the root canal there are essentially no voids in the root canal.

In some embodiments, a method of treating pulpal damage includes generating a three-dimensional image of a root canal. The method also includes manufacturing the customized root canal obturation core based on the three-dimensional image of the root canal. The customized root canal obturation core has a contour that closely matches a contour of the root canal. The method further includes inserting the customized root canal obturation core into the root canal such that there are essentially no voids in the root canal.

In some embodiments, a system for generating a customized root obturation core includes a computational device comprising a processor configured to extract three-dimensional data from a three-dimensional image of a root canal. The system also includes a computer controlled system configured to manufacture the customized root canal obturation core using the extracted three-dimensional data.

In some embodiments, a root canal includes an apical portion, a middle portion, and a coronal portion and a customized core for obturating the root canal includes a pre-formed single-piece body shaped to match a contour of the root canal. When the pre-formed single-piece body is inserted in the root canal, the pre-formed single-piece body substantially fills the apical portion, the middle portion, and the coronal portion of the root canal, forming a seal substantially impervious to bacteria and tissue fluid in the root canal.

In some embodiments, the root canal defines a non-uniform contoured volume. In some embodiments, the pre-formed single-piece body is generated by a computer controlled manufacturing system based on a three-dimensional image of the root canal.

In some embodiments, the pre-formed single-piece body includes a biocompatible material. In some embodiments, the biocompatible material is dimensionally stable. In some embodiments, the pre-formed single-piece body includes an antimicrobial material. In some embodiments, the pre-formed single-piece body includes a material that is substantially impervious to bacterial and tissue fluid infiltration.

In some embodiments, the pre-formed single-piece body includes a radiopaque material. In some embodiments, the pre-formed single-piece body includes a material that expands when exposed to a catalyst. In some embodiments, the material that expands when exposed to a catalyst remains dimensionally stable after expansion. In some embodiments, an expansion ratio of the material varies along a length of the pre-formed single-piece body. In some embodiments, at least a portion of the pre-formed single-piece body is a non-dentin color.

In some embodiments, the pre-formed single-piece body includes a handle that extends into the root canal chamber, formed at a coronal end of the pre-formed single-piece body. In some embodiments, the handle includes an interface configured to cooperatively engage with a removal tool configured to remove the pre-formed single-piece body from the root canal.

In some embodiments, an exterior surface of the pre-formed single-piece body is smooth such that the exterior surface does not bond to a sealant between the pre-formed single-piece body and the root canal. In some embodiments, the exterior surface of the pre-formed single-piece body is hydrophobic. In some embodiments, the exterior surface of the pre-formed single-piece body has a coefficient of friction within a range of about 0.0 to about 0.15. In some embodiments, the exterior surface of the pre-formed single-piece body includes polytetrafluoroethylene (PTFE). In some embodiments, an exterior surface of the pre-formed single-piece body is rough such that the exterior surface creates a mechanical interlock with any sealant in the root canal.

In some embodiments, the pre-formed body is made of a hydrophilic material.

In some embodiments, an exterior surface of the pre-formed single-piece body includes a biocompatible and bioactive material. In some embodiments, the biocompatible and bioactive material includes calcium silicate. In some embodiments, the pre-formed single-piece body includes a material that dissolves when exposed to a solvent.

In some embodiments, a density of the pre-formed single-piece body varies along a width of the pre-formed single-piece body. In some embodiments, the pre-formed single-piece body defines a conductive pathway from an apical end to a coronal end of the pre-formed single-piece body. In some embodiments, the pre-formed single-piece body defines a conductive pathway from an apical end to a point at the coronal end of the handle.

In some embodiments, a customized core for obturating a root canal defining a non-uniform contoured volume includes a pre-formed body shaped to match at least an apical portion of the non-uniform contoured volume. When the pre-formed body is inserted in the root canal, the pre-formed body substantially fills the apical portion of the non-uniform contoured volume, forming a seal substantially impervious to bacteria and tissue fluid in the apical portion of the non-uniform contoured volume of the root canal.

BRIEF DESCRIPTION OF THE DRAWINGS

Embodiments will now be described, by way of example only, with reference to the accompanying schematic drawings in which corresponding reference symbols indicate corresponding parts, and in which:

FIGS. 1A and 1B illustrate (1) a coronal view of a human anterior tooth and (2) a sagittal view of the human anterior tooth of FIG. 1A, respectively.

FIGS. 2A and 2B illustrate (1) a coronal view of an abscessed human anterior tooth and (2) a sagittal view of the human anterior tooth of FIG. 2A, respectively.

FIG. 5 illustrates an exemplary tooth testing matrix.

Figure 3:
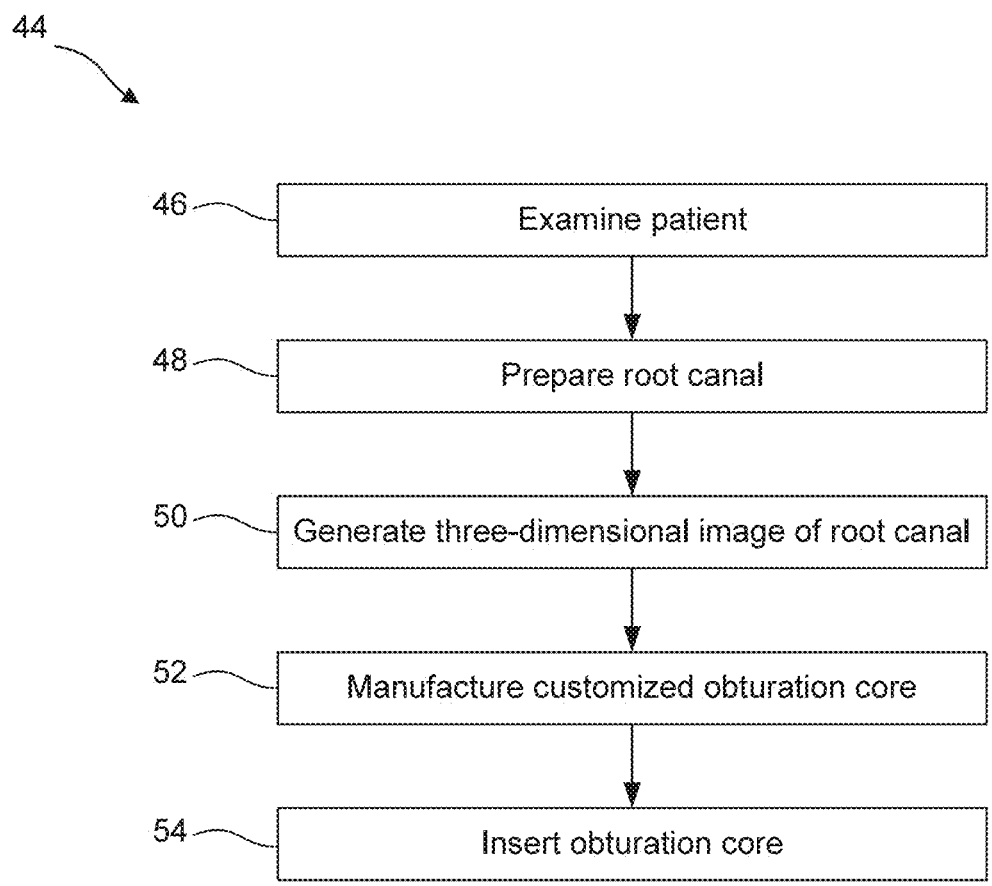
FIG. 3 illustrates a block diagram of a method of treating pulpal damage according to an embodiment.

Features and advantages of the embodiments of the present invention will become more apparent from the detailed description set forth below when taken in conjunction with the drawings.

DETAILED DESCRIPTION

While the invention is described herein with reference to illustrative embodiments for particular applications, it should be understood that the invention is not limited thereto. Those skilled in the art with access to the teachings provided herein will recognize additional modifications, applications, and embodiments within the scope thereof and additional fields in which the invention would be of significant utility.

FIGS. 1A and 1B illustrate a coronal view of a human anterior tooth 10 and a sagittal view of tooth 10, respectively. Tooth 10 includes a root 11 that defines a root canal 12 that contains a pulp 14. Pulp 14 is soft tissue that includes blood vessels, connective tissue, and nerves. Pulp 14 can extend from a physiologic apex 16, which is usually located about 0.5 mm from a radiographic apex 18, to a pulp horn 20 at a crown 22 of tooth 10. Crown 22 is typically composed of dentin 24 and a layer of enamel 26 that covers dentin 24. Root canal 12 can include a coronal portion 28 (the portion nearest crown 22), a middle portion 30, and an apical portion 32 (the portion nearest physiological apex 16), extending from crown 22 to physiological apex 16.

FIGS. 2A and 2B illustrate (1) a coronal view of an abscessed human anterior tooth 34 and (2) a sagittal view of tooth 34, respectively. Sometimes bacteria and/or tissue fluid 36 is introduced into pulp 14 in root canal 12. For example, bacteria and/or tissue fluid 36 can be introduced by caries 38 in tooth 34, periodontal disease, or a fracture. Sometimes bacteria and/or tissue fluid 36 causes inflammation or infection in the surrounding bone, for example, in close approximation to a lateral or accessory canal 40 or to a physiologic terminus 42 of canal 12. Inflammation or infection can cause pain and swelling. Damage to pulp 14 may also occur even if the tooth has no visible deterioration, for example, caries 38. Once pulp 14 becomes inflamed or infected, a root canal or extraction can be necessary to remove the affected tissue and to restore the area back to health.

FIG. 3 illustrates a block diagram of a method 44 for treating pulpal damage according to an embodiment.

Method 44 includes a patient examination step 46, a root canal preparation step 48, a three-dimensional image generation step 50, an obturation core manufacturing step 52, and an obturation core insertion step 54.

Figure 4:
FIG. 4 is an exemplary periapical radiograph of a maxillary left central incisor.

In some embodiments, at patient examination step 46, a dentist, for example, a general dentist or an endodontist, conducts an examination of the patient. During the examination, the dentist can interview the patient and review the patient medical and dental history. In some embodiments at step 46, the dentist exposes a planar—two-dimensional— radiographic image of the tooth or teeth of interest. FIG. 4 is an exemplary periapical radiographic image of a maxillary left central incisor that could be obtained during the exam. The dentist can evaluate the planar radiographic image and then perform a physical examination.

In some embodiments at step 46, the physical examination includes recording responses to various tests including, for example, percussion, palpation, bite stick, thermal, transillumination, and electrical pulp tests. During the physical examination, the dentist can test for signs of pulpal damage, for example, pain on percussion, sensitivity to hot or cold, color changes, soreness, or swelling in the surrounding tissues. These results can be recorded as objective findings in a written matrix such as the one illustrated in FIG. 5. As shown in FIG. 5, the results recorded in the matrix indicate that tooth #9, the maxillary left central incisor, may be infected.

Figure 6:
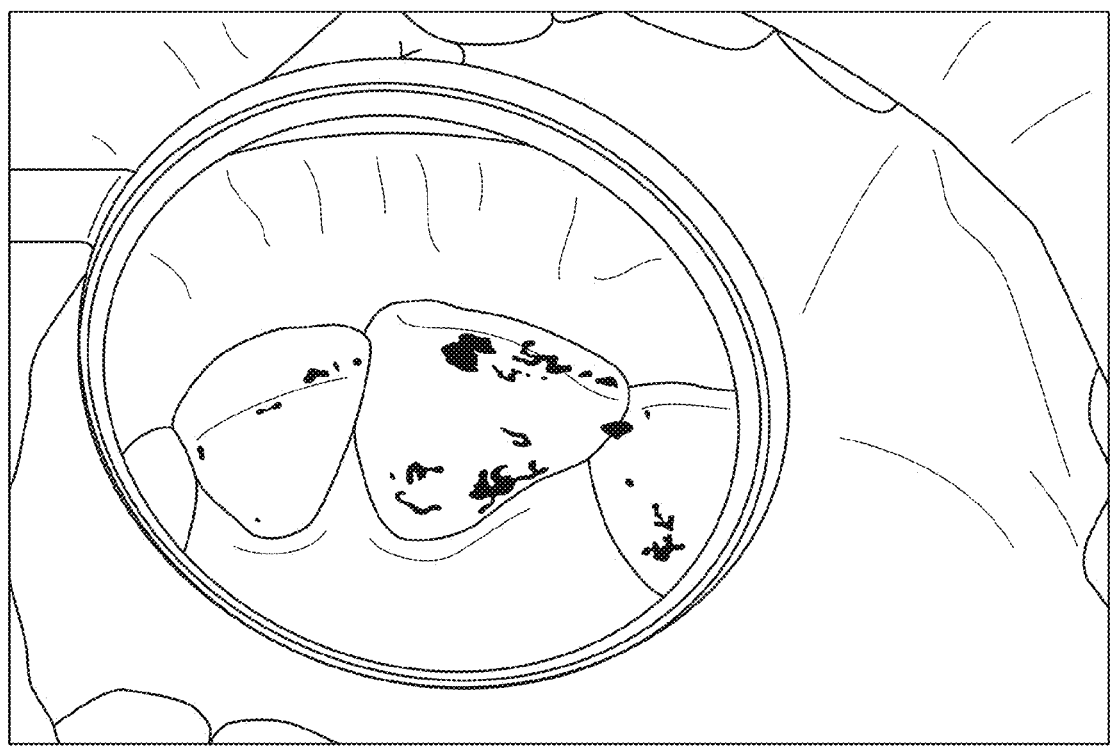
FIG. 6 is a photograph of a central incisor to document the visible light findings and occlusion.

In some embodiments, patient examination step 46 also includes an examination of the tooth or teeth of interest for fracture, for example, by using an explorer, special lighting, and/or using enhanced magnification. In some embodiments, patient examination step 46 also includes an examination of the tooth or teeth of interest for hyper-occlusion. FIG. 6 shows a pre-treatment photographic image that may be exposed to document the examination findings, for example, hyper-occlusion.

Figures 7A, 7B, 7C:
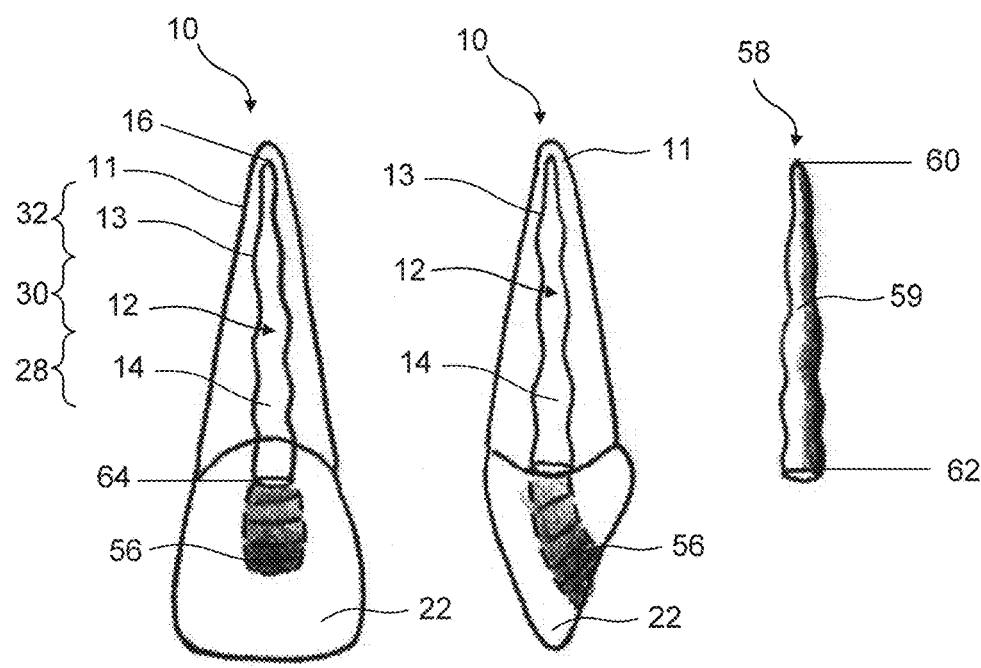
FIGS. 7A, 7B, and 7C illustrate (1) a coronal view of a human anterior tooth after irrigation and cleaning and after minimal or no instrumentation; (2) a sagittal view of the human anterior tooth of FIG. 7A; and (3) a customized obturation core according to an embodiment, respectively.
Figures 8A, 8B, 8C:
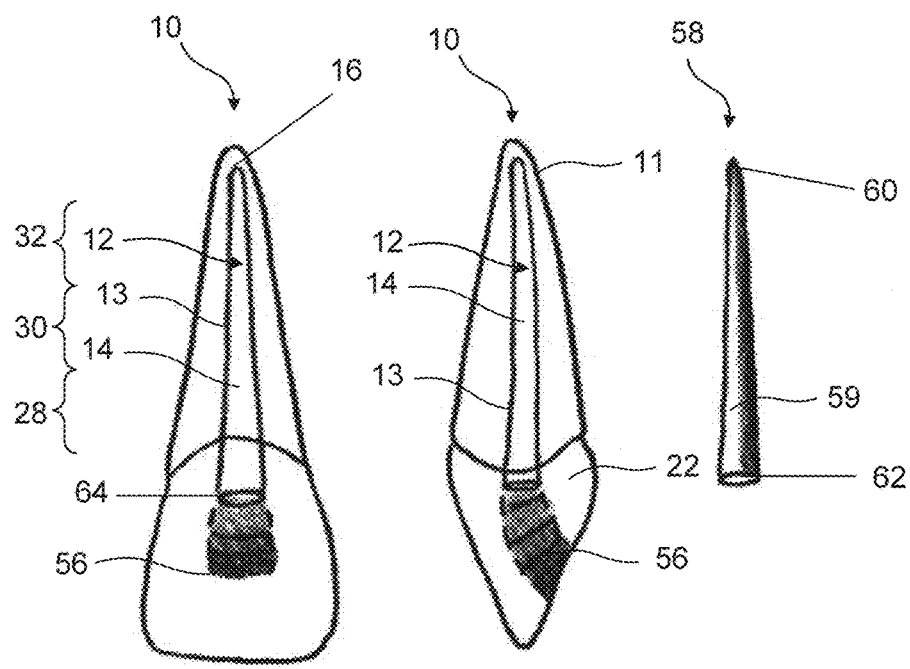
FIGS. 8A, 8B, and 8C illustrate (1) a coronal view of a human anterior tooth after irrigation and cleaning and after instrumentation; (2) a sagittal view of the human anterior tooth of FIG. 8A; and (3) a customized obturation core according to an embodiment, respectively.

Method 44 can also include a root canal preparation step 48. At step 48, the dentist can prepare root canal 12 of tooth 10. In some embodiments, root canal preparation step 48 includes a routine non-surgical procedure for removing pulp 14 from canal 12, for example, through an access opening 56 (referring to FIGS. 7A, 7B, 8A, and 8B) on an exposed surface of tooth 10 in some embodiments. In some embodiments at step 48, after removing pulp 14, root canal 12 is irrigated and disinfected, for example, by providing an irrigant to remove substantially all traces of tissue, debris, bacteria, and tissue fluid in root canal 12. For example, canal 12 can be irrigated using a needle that delivers the irrigant. In some embodiments at step 48, as shown in FIGS. 7A and 7B, after irrigating and disinfecting, walls 13 (which form the contour of canal 12) of canal 12 are either uninstrumented or lightly instrumented through access opening 56 using for example, a sonic, multisonic or ultrasonic agitator, a laser technique, or any combination thereof. In some embodiments at step 48, as shown in FIGS. 8A and 8B, after irrigating and disinfecting, the walls of canal 12 are moderately or heavily instrumented so that walls 13 of canal 12 form a desired shape. For example, as shown in FIGS. 8A and 8B, walls 13 of canal 12 form a conical shape. In some embodiments, the desired shape of walls 13 of canal 12 is a non-conical shape.

In some embodiments, root canal preparation step 48 includes a revision procedure. That is, root canal 12 is retreated or revised because of continued infection after initial treatment, which can sometimes occur years later. Revision procedures can be necessary when there was an incomplete prior root canal therapy, complicated canal anatomy, or contamination with oral bacteria and/or tissue fluid through a leaking restoration. In some embodiments in which root canal preparation step 48 is a revision procedure, the previously placed root canal filling material is removed from canal 12, and canal 12 is irrigated and disinfected. In some embodiments in which root canal preparation step 48 is a revision procedure, root canal preparation step 48 is performed using an operating microscope along with digital radiography.

In some embodiments, root canal preparation step 48 is a surgical procedure that includes, for example, surgically removing infected root 11 or apex 16 and the surrounding tissue. This procedure is known as apical micro-surgery or an apicoectomy. A surgical operating microscope with special coaxial lighting can be used to enhance visualization during such procedures.

Method 44 can also include a three-dimensional image generation step 50. At step 50, a three-dimensional image that includes, at least in part, canal 12 is generated. In some embodiments, the three-dimensional image is a high-resolution three-dimensional image, for example, an image having a resolution in the range of about 75-90 µm voxel size. In some embodiments, the three-dimensional image has a resolution outside of the range of about 75-90 µm voxel size.

In some embodiments at image generation step 50, one or more three-dimensional images are generated.

Figure 9A:
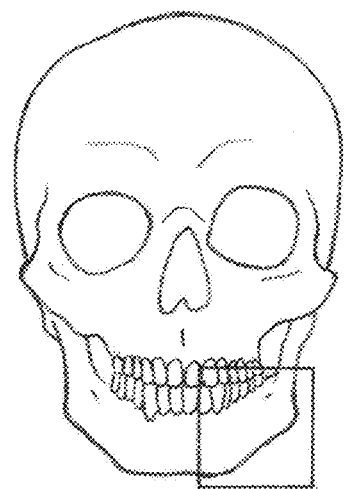
FIGS. 9A, 9B, and 9C illustrate a schematic view of a human skull with, from the left, a limited field of view, a medium field of view, and a large field of view, respectively, according to an embodiment.
Figure 9B:
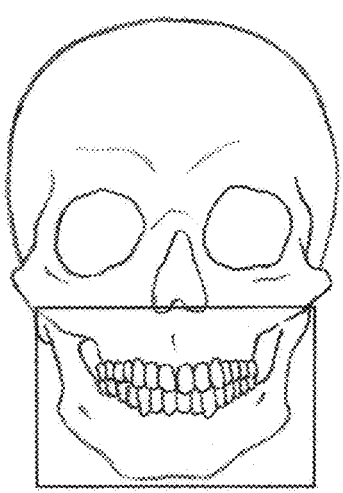
Figure 9C:
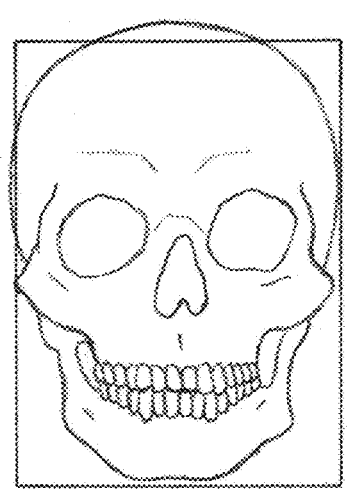
Figure 10A:
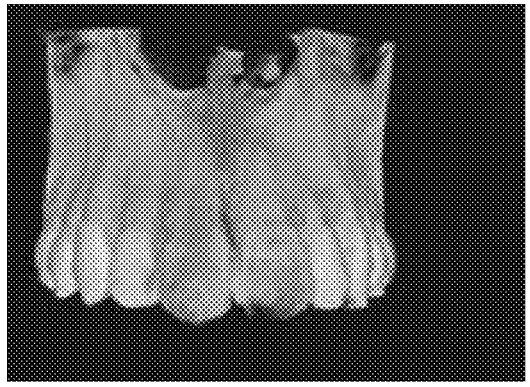
FIGS. 10A-10D illustrate exemplary generated three-dimensional images.
Figure 10B:
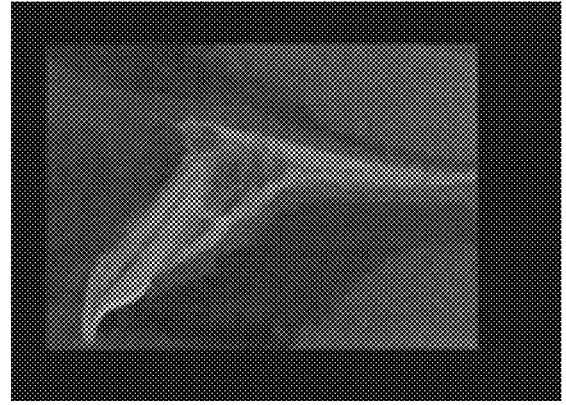
Figure 10C:
Figure 10D:
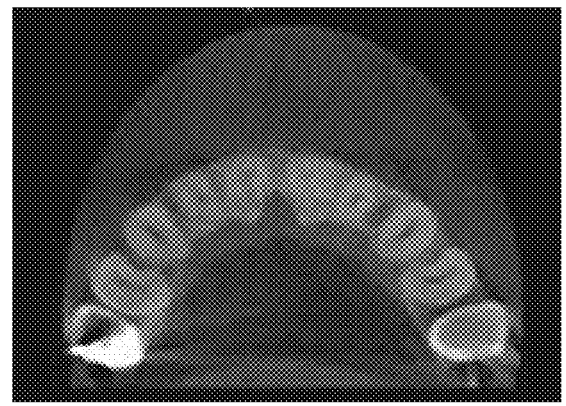

In some embodiments, the three-dimensional image is a tomographic image. In some embodiments, the three-dimensional image is generated by computed tomography (CT), for example, using X-ray CT such as a cone-beam CT (CBCT), magnetic resonance imaging (MRI), ultrasound, radiography, optical imaging, or any other suitable three-dimensional imaging technology. The three dimensional image may have various fields of view (FOV). For example, as shown in FIGS. 9A-9C, the generated three-dimensional image may have a limited FOV as illustrated by the box in FIG. 9A, a medium FOV as illustrated by the box in FIG. 9B, or a large FOV as illustrated by the box in FIG. 9C. FIGS. 10A-10D illustrate exemplary generated three-dimensional images showing a view of the reconstructed surface in FIG. 10A, a reconstructed sagittal view in FIG. 10B, a reconstructed coronal view in FIG. 10C, and an axial view in FIG. 10D, according to an embodiment. The generated three-dimensional image can show a single tooth, a quadrant of teeth, a sextant of teeth, or the entire dentition and surrounding structures in three dimensions in some embodiments.

In some embodiments, the three-dimensional image is generated intra-operatively and post-operatively—concurrently with or after canal preparation step 48.

In some embodiments, image generation step 50 is performed at a dentist's office. In some embodiments, step 50 is performed at a facility outside of the dentist's office.

Method 44 can also include an obturation core manufacturing step 52. At step 52, a customized obturation core 58 is made. FIGS. 7C and 8C illustrate exemplary obturation cores 58. In some embodiments at step 52, a single-piece body 59 of obturation core 58 is shaped so its preformed contour (i.e., its contour before being inserted into canal 12) closely matches the contour of walls 13 of root canal 12. In some embodiments, the contour of body 59 of core 58 closely matches the contour of walls 13 of root canal 12 such that substantially the entire canal 12 is filled with only core 58 when inserted therein—there are essentially no voids in canal 12 at coronal portion 28, middle portion 30, and apical portion 32. As used in this application, essentially no voids in the canal means that the gap between any portion of core 58 and walls 13 of root canal 12 is smaller than at least about 2.0 micrometers—the average size of bacterium. In some embodiments, the gap between any portion of core 58 and walls 13 of root canal 12 is smaller than about 0.5 micrometers. In some embodiments, the contour of body 59 of core 58 closely matches the contour of walls 13 of root canal 12 such that substantially the entire canal 12 is filled with core 58 and a sealant when inserted therein—there are essentially no voids in canal 12 at coronal portion 28, middle portion 30, and apical portion 32.

In some embodiments, the contour of body 59 of core 58 is substantially parallel to the contour of root canal 12. In some embodiments, core 58 has an initial volume of about 90 to 110 percent of the volume of root canal 12. In some embodiments, core 58 has an initial volume of about 95 to 105 percent of the volume of root canal 12. For example, as shown in FIG. 7C, body 59 of core 58 has a wavy contour that closely matches the wavy contour of walls 13 of canal 12 in FIGS. 7A and 7B. As shown in FIG. 8C, body 59 of core 58 has a substantially conical contour that closely matches the conical contour of walls 13 of canal 12 in FIGS. 8A and 8B. In some embodiments, core 58 has a preformed shape that includes an intermediate portion that has a smaller diameter than proximal and distal portions of core 58, for example, an hour-glass shape.

Figure 16C:
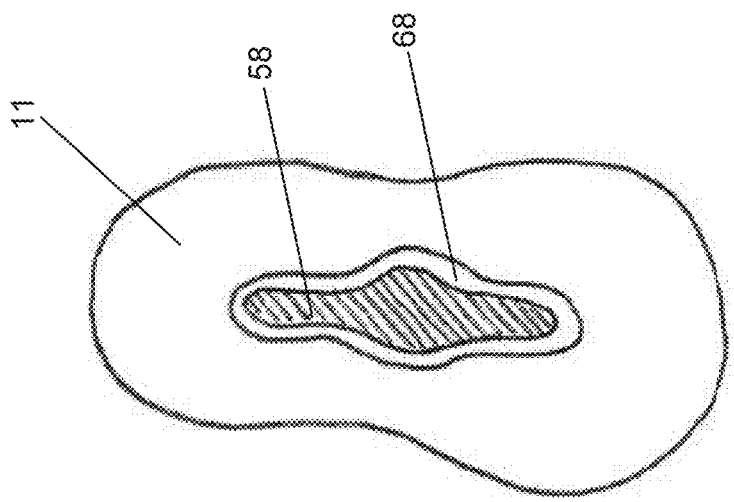
FIGS. 16A, 16B, and 16C illustrate cross-sectional views of a root and root canal after instrumentation and disinfection with no core and sealant, with a conventional core and sealant, and a customized obturation core and sealant according to an embodiment, respectively.
Figure 16B:
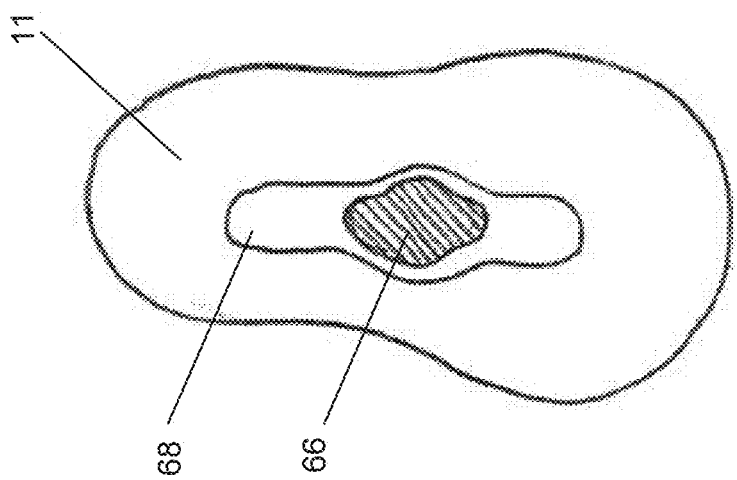
Figure 16A:
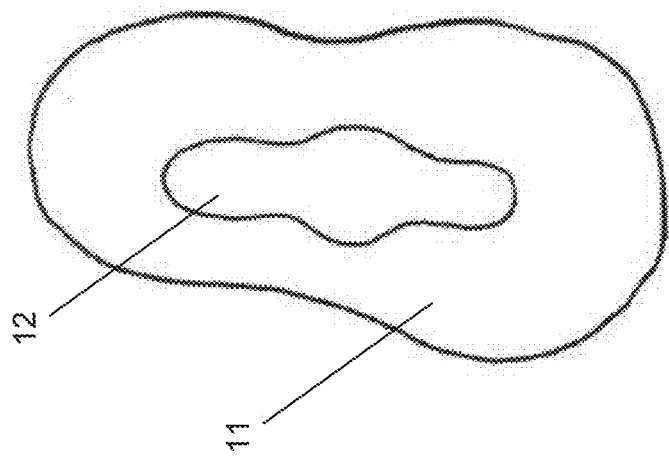

In some embodiments in which core 58 is used with a sealant, core 58 is sized to minimize the volume of sealant used relative to a conventional obturation core that uses a sealant. For example, referencing FIGS. 16A, 16B, and 16C which illustrate cross-sectional views of root 11 and root canal 12 (1) with no core and sealant, (2) with a conventional core 66 and sealant 68, and (3) with customized obturation core 58 and sealant 68 according to an embodiment, respectively, the volume of sealant 68 required to entirely fill canal 12 with core 58 such that there are essentially no voids in canal 12 is less than the volume of sealant 68 required to fill canal 12 with conventional core 66. Reducing the volume of sealant 68 required to fill canal 12 reduces the risk that sealant 68 will deteriorate and, thus, allow bacteria and/or tissue fluid to infiltrate canal 12.

In some embodiments, a postoperative radiograph of a tooth using customized core 58 will have a better radiographic appearance than a tooth using a conventional core 66. That is, because of the close-fit of core 58, the filled root canal 12 will have a better appearance that indicates the highly accurate fitting of core 58 to canal walls 13.

In some embodiments, as shown in FIGS. 7A, 7C, 8A, and 8C, core 58 has a length such that, when core 58 is inserted in canal 12, an apical end 60 of core 58 is positioned at physiologic apex 16, and a coronal end 62 of core 58 is positioned at the orifice 64 of canal 12. In other embodiments, core 58 has a length such that, when core 58 is inserted in canal 12, apical end 60 is positioned at physiologic apex 16, and coronal end 62 is positioned proximate to access opening 56.

In some embodiments, obturation core 58 is made of a sterile material. In some embodiments, obturation core 58 is an inert material. In some embodiments, obturation core 58 is a biocompatible material. In some embodiments, obturation core 58 is a sterile, inert, and biocompatible material. In some embodiments, obturation core 58 is made of a sterile, inert, and/or biocompatible material. In some embodiments, core 58 is made of a material that is antimicrobial to reduce the risk that bacteria will grow in canal 12. In some embodiments, core 58 is made of a material that is substantially impervious to bacterial and tissue fluid infiltration. In some embodiments, core 58 is made of a material that can be safely applied to avoid overextension into vital anatomic structures. In some embodiments, obturation core 58 is a biocompatible material that is dimensionally stable. In the context of this application, "dimensionally stable," means that the dimensions and shape of obturation core 58 do not shrink after final placement in canal 12. In some embodiments, core 58 is made of a material that is radiopaque. In some embodiments, the obturation core 58 comprises gutta percha, nylon, plastic, or any other material of a desired level of cleanliness, biocompatibility, inertness, and inherent antimicrobial activity.

In some embodiments, obturation core 58 is either made of or coated with a bioactive and biocompatible material configured to promote dentin remineralization and adhesion to the root canal surface. In some embodiments, the bioactive and biocompatible material can include calcium silicate, for example, tri-calcium silicate or di-calcium silicate. In some embodiments, the material includes nanosynthesized calcium silicates, which can vary in shape and topography which in turn changes the level of bioactivity.

In some embodiments, obturation core 58 is either made of or coated with a material including a radiopacifier to improve image contrast and visualization of obturation core 58 in tomographic and planar images generated by, for example, computed tomography (CT) such as cone-beam computed tomography (CBCT), intraoral radiographic imaging, magnetic resonance imaging, or ultrasonic imaging. For example, the radiopacifier can be bismuth oxide ($Bi2O3$), ytterbium trifluoride ($YbF3$), or zirconium oxide ($ZrO2$).

In some embodiments, obturation core 58 is a non-dentin color configured to allow a dentist to easily identify obturation core 58 relative to root canal 12, for example, red, orange, blue, white, or some other dentin contrasting color. In some embodiments, at least a portion of obturation core 58 is a non-dentin color. For example, coronal end 62 can be a non-dentin color. The non-dentin color allows a dentist to easily identify and distinguish obturation core 58 from the surrounding tooth structure during, for example, a retreatment procedure.

In some embodiments, obturation core 58 can have a smooth exterior surface configured to not bond to a sealant to allow a dentist to easily manipulate and remove obturation core 58 relative to root canal 12 during, for example, a retreatment procedure in which obturation core 58 is removed from root canal 12. For example, the exterior surface of obturation core 58 can have a coefficient of friction within a range of about 0.0 to about 0.15. In some embodiments, the entire obturation core or the exterior surface of obturation core 58 can be made of a hydrophobic material, for example, polytetrafluoroethylene (PTFE), to help ensure that the surface does not bond to any sealant.

In some embodiments, obturation core 58 can have a rough exterior surface that creates a mechanical interlock with any sealant in root canal 12. The mechanical interlock between rough exterior surface of obturation core 58 and the sealant in root canal 12 can help form a seal and prevent bacterial and tissue fluid infiltration. In some embodiments, entire obturation core or the exterior of the obturation core can be made of a hydrophilic material to help ensure, for example, that the surface bonds to a sealant or that obturation core 58 absorbs an expansion catalyst.

In some embodiments, the exterior surface of the obturation core 58 is treated with a material that can help form a seal and prevent bacterial and tissue fluid infiltration.

In some embodiments, obturation core 58 comprises an expansive biocompatible material. For example, obturation core 58 can be made from a material that expands when exposed to a catalyst, for example, moisture or a sealant for cementing core 58 to tooth 10. In such embodiments, obturation core 58 is manufactured such that upon expansion in situ obturation core 58 achieves about 100 percent or more than about 100 percent of the volume of root canal 12 such that with sealer there are essentially no voids in canal 12. In some embodiments, obturation core 58 is a material that expands when exposed to a catalyst and remains dimensionally stable after expansion. For example, after expansion in situ in canal 12, the dimensions and shape of obturation core 58 do not shrink. In some embodiments, the expansion ratio of core 58 is constant along the length of core 58. Notably, although the expansion ratio may be constant along the length of core 58, the absolute diametric expansion may vary depending upon the initial preformed diameter of core 58. For example, if core 58 has a 105 percent diametric expansion ratio and the initial shape of core 58 has a 2 mm diameter bottom and a 10 mm diameter top, the bottom diameter will expand 0.1 mm, and the top diameter will expand 0.5 mm. In other embodiments, different longitudinal segments of core 58 can have different expansion ratios. Thus, for example, the distal segment can be configured to have a higher expansion ratio than the proximal segment. Likewise, the proximal segment can be configured to have a higher expansion ratio than the distal segment. Due to the variable dimensions of a patient's root canal, it is understood that the diameter and shape of the obturation core would vary along its length to match the imaged shape of the patient's root canal. It is also understood that an expansive material having different diameters along its length will expand differently.

In some embodiments, obturation core 58 comprises a non-expansive material.

In some embodiments, obturation core 58 comprises a material that does not diametrically contract over an extended period of time, for example, at least 10 years, at least 20 years, at least 30 years, or a lifetime.

In some embodiments, the density of the material forming obturation core 58 varies within obturation core 58. In some embodiments, the density can vary along a width of obturation core 58. For example, obturation core 58 can have a hard outer shell that encases a soft, less dense inner core. In such a configuration, the soft inner core can be easily drilled out with, for example, a rotary drill, while the hard outer shell guides the drill along the root canal. In some embodiments, obturation core 58 can have a linearly varying density in the radial direction. In some embodiments, obturation core 58 can have a non-linearly varying density in the radial direction. In some embodiments, the exterior surface at coronal end 62 includes a portion made of a lower density material. In some embodiments, the density can vary along a vertical length of obturation core 58.

In some embodiments at step 52, obturation core 58 is manufactured by a system comprising a computational device comprising a processor configured to generate a three-dimensional CAD model of either canal 12 or body 59 of core 58, and a computer controlled manufacturing system. The computational device can be, for example, a computer, a PDA, a tablet, or any other suitable computational device comprising a processor.

The computer controlled manufacturing system can be, for example, a computer numerically controlled machine, an additive manufacturing machine, or any other suitable manufacturing machine. In some embodiments in which the computer controlled manufacturing system is a computer numerically controlled machine, the computer numerically controlled machine can include a lathe, a milling device, or any other subtractive machine. In some embodiments in which the computer controlled manufacturing system is an additive manufacturing machine, the additive manufacturing machine can be a stereolithographic machine, an inkjet printer machine (i.e., a 3D printer), a selective laser sintering machine, a fused deposition modeling machine, or any other suitable additive machine.

In some embodiments, the computer controlled manufacturing system manufactures core 58 using the three dimensional image obtained at step 50. For example, the three dimensional image generated at step 50 can be uploaded to the computational device using computer imaging software and stored in memory on the computational device. The computational device can generate a three-dimensional CAD model of canal 12 or of body 59 of core 58 by using the uploaded three-dimensional image. In some embodiments, the three-dimensional CAD model is made by decomposing root canal 12 into cross-sectional layer representations. In some embodiments, the computational device uses the three-dimensional CAD model to generate instructions, for example, numerical files, that drive the computer controlled system to manufacture body 59 of core 58, and then the computational device transmits the instructions to the computer controlled manufacturing system. In some embodiments, the computational device is separate from the computer controlled system. In some embodiments, the computational device is integral with the computer controlled system.

Figure 11:
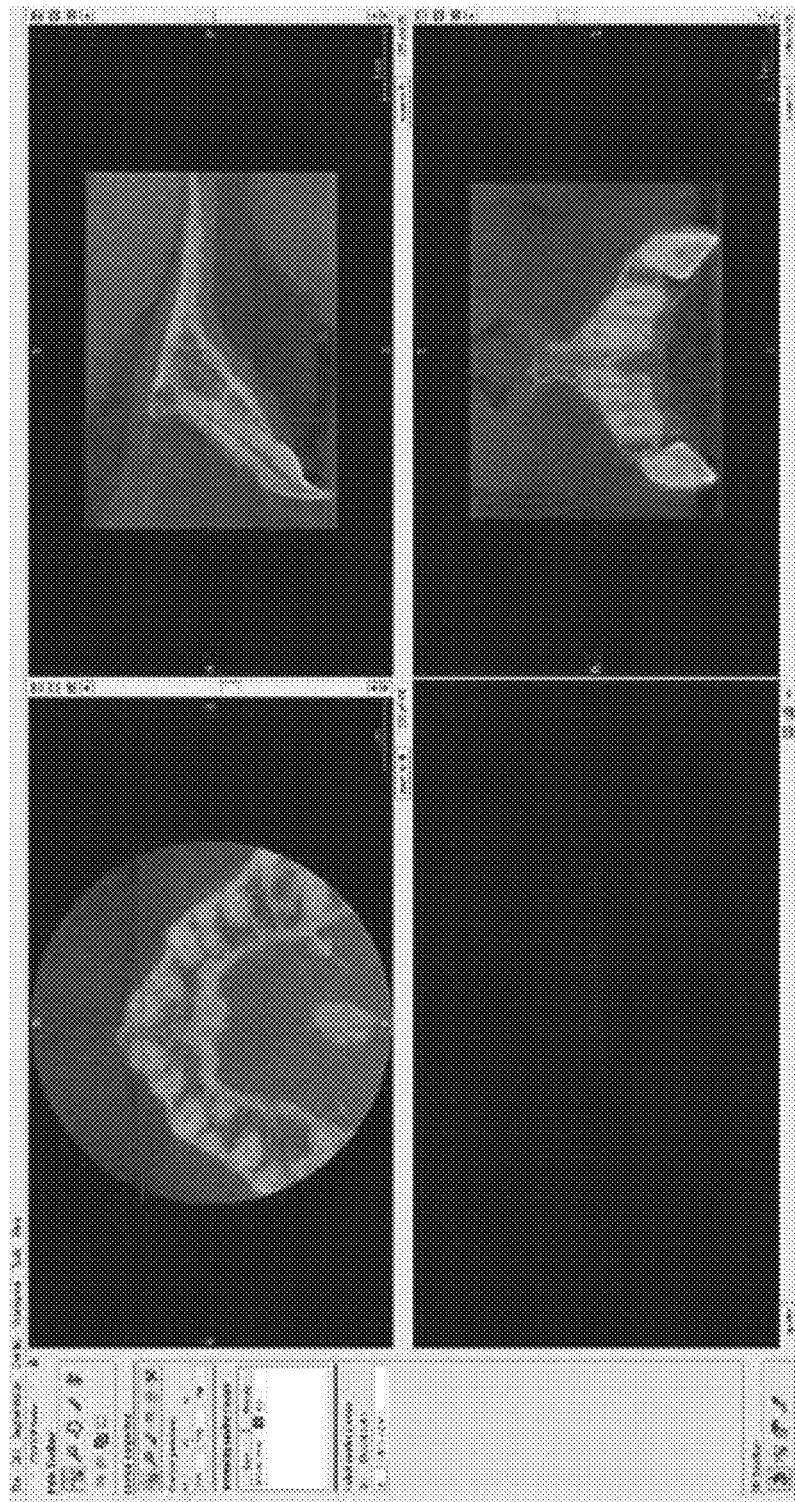
FIGS. 11-15 illustrate screen shots of exemplary imaging software used to segment a three-dimensional image and to render a volumetric analysis of the root canal.
Figure 12:
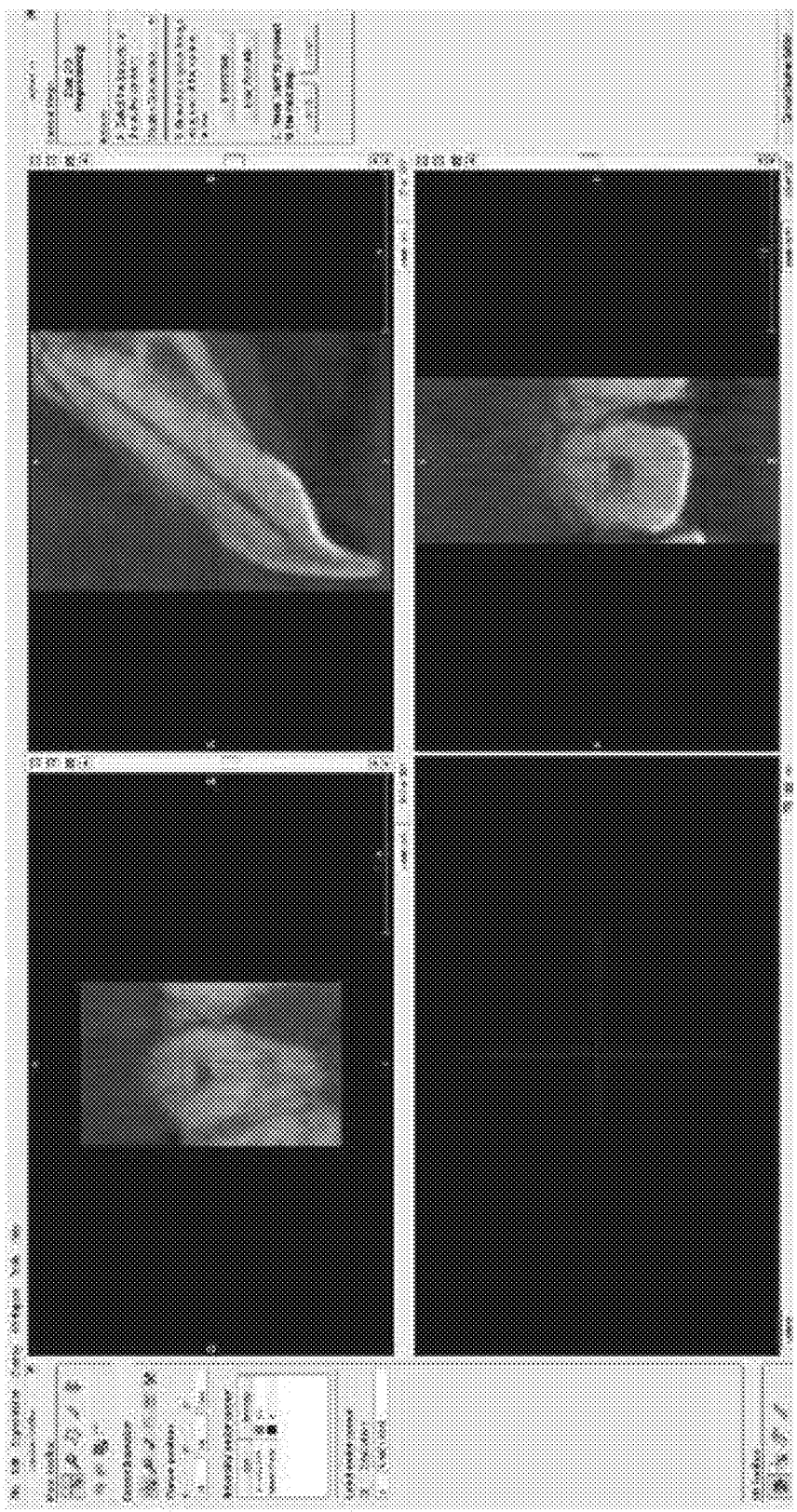
Figure 13:
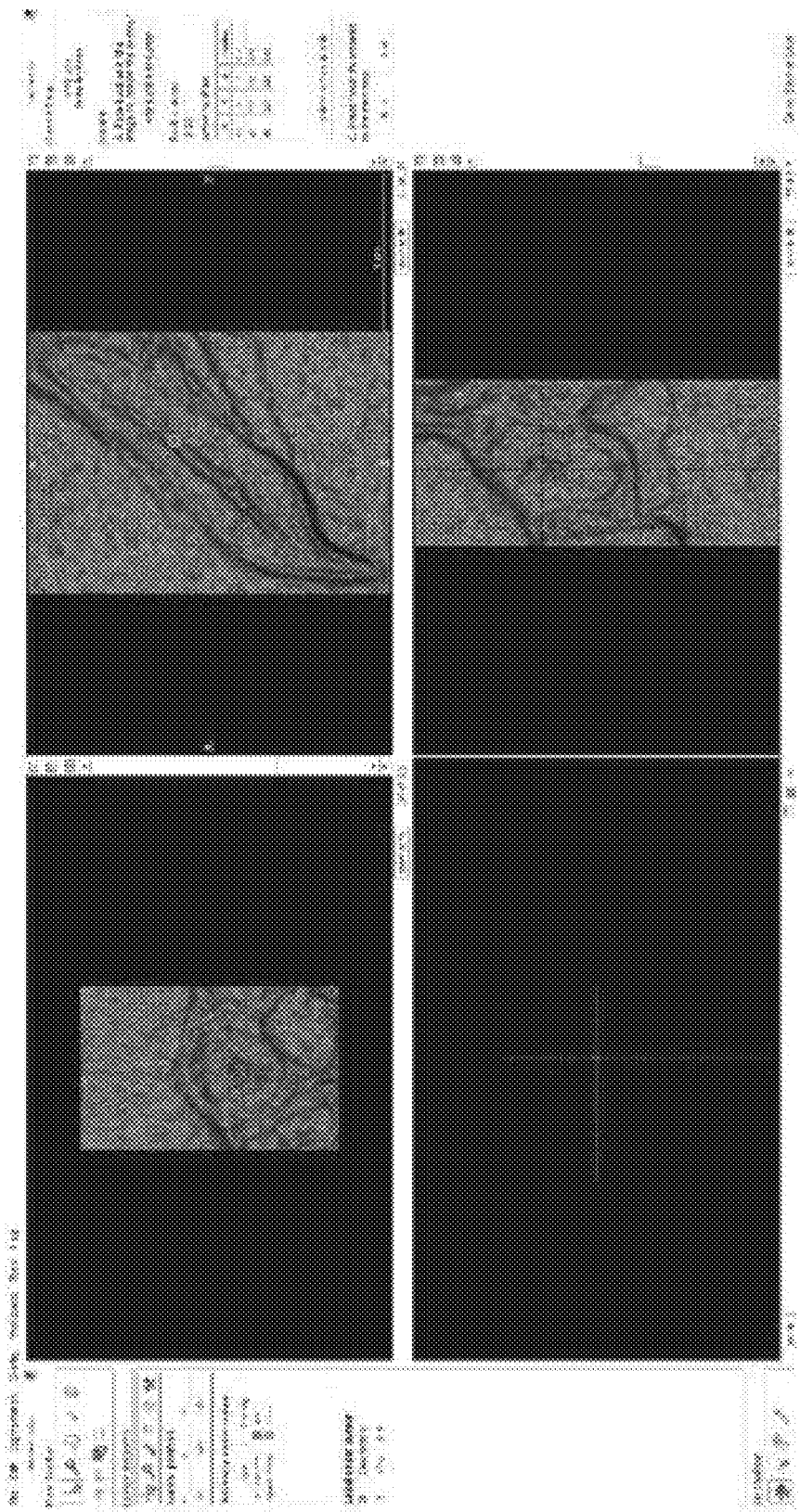

FIGS. 11-15 illustrate screen shots of exemplary imaging software running on the computational device for generating a three-dimensional CAD model of canal 12 or body 59 of core 58. Particularly, FIG. 11 illustrates a step of uploading the generated three-dimensional image to the computational device. Using the software, a user can identify, for example, by outlining, a region of interest of tooth 10, for example, canal 12, on a graphical user interface on a display of the computational device as illustrated in FIG. 12. Then in some embodiments, the software generates a three-dimensional CAD model of canal 12. For example, FIG. 13 illustrates an exemplary screen shot for adjusting the automatic segmentation tool for performing the segmentation iterations with appropriate landmarks applied to generate a three-dimensional CAD model of canal 12 (or core 58). In some embodiments, the software simply and quickly automatically segments root canal 12 and highlights the lateral or accessory canals.

Figure 14:
Figure 15:
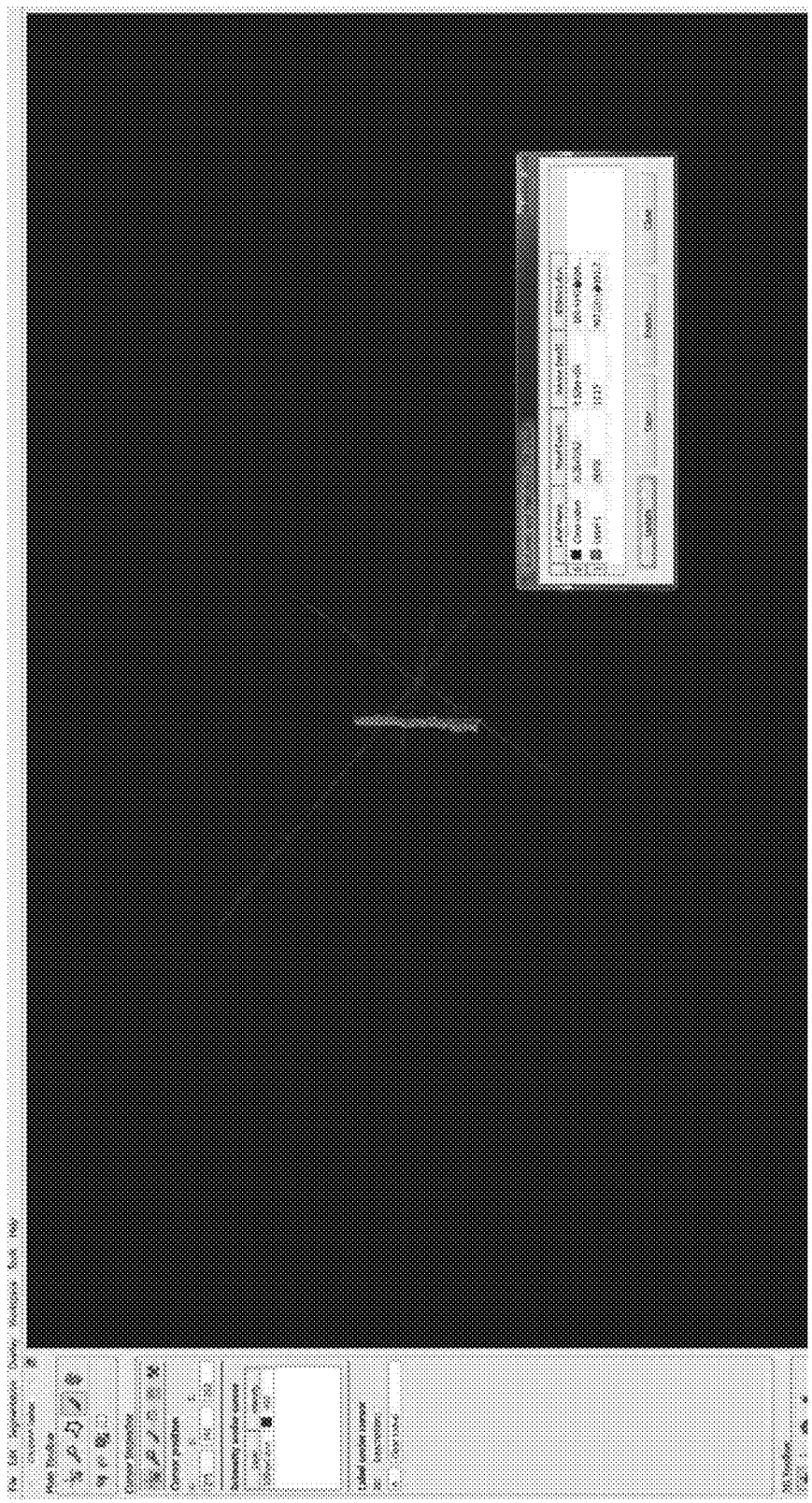

In some embodiments, this CAD model generation sub-step includes measuring the length and width of canal 12. In some embodiments, the length of canal 12 is measured from physiological apex 16 to access opening 56. In other embodiments, the length of canal 12 is measured from physiological apex 16 to orifice 64 of the canal 12. FIG. 14 illustrates an exemplary screen shot of the graphical user interface for measuring the length and width of canal 12. In some embodiments, the width and length of canal 12 is determined in a slice-by-slice format, for example, by using voxel count and volume. The software then generates a three-dimensional CAD model of canal 12 or body 59 of core 58. FIG. 15 illustrates an exemplary three-dimensional CAD model of body 59 of core 58. From the three-dimensional CAD model, the computational device can generate the file(s) for driving the computer controlled manufacturing system, for example, number files, to make core 58.

In some embodiments, the software superimposes core 58 within canal 12 to allow a user to assess how core 58 fills canal 12 and to verify that core 58 fills the entire canal 12 without forming voids.

In some embodiments core generation step 52 occurs at the dentist's office. In some embodiments, core generation step 52 occurs at a facility off-site from dentist's office, and core 58 is shipped to the dentist.

After generating core 58 at step 52, a dentist inserts core 58 within canal 12 at step 54 of method 44. In some embodiments, core 58 is inserted in canal 12 without using a sealant. In some embodiments, core 58 is inserted in canal 12 with a sealant to cement core 58 to tooth 10. In some embodiments in which a sealant is used, canal 12 is coated with sealant before inserting core 58 into canal 12, core 58 is coated with sealant, or both. In some embodiments, when core 58 is inserted into canal 12 with or without using sealant, canal 12 is fully sealed without voids. In some embodiments, a sealant is used to cement core 58 to canal 12. In some embodiments, when inserted, core 58 renders canal 12 substantially impervious to bacterial and tissue fluid infiltration or entombs any remaining bacteria in canal 12.

In some embodiments, step 52 also includes placing a permanent restoration in access opening 56 to seal core 58 within canal 12.

In some embodiments, core 58 can be inserted into canal 12 with minimal force, for example, because the preformed contour of body 59 of core 58 closely matches the contour of canal 12. Accordingly, the risk of tooth fracture can be minimized.

In some embodiments, one or more of steps 46, 48, 50, and 52 are omitted from method 44. For example, steps 46 and 52 may be omitted.

In some embodiments, obturation core 58 can include an electrical conducting pathway such that obturation core 58 can be used as the probe for an electronic apex locator (EAL) device. In some embodiments, the electrical conducting pathway can extend between apical end 60 and coronal end 62 or the coronal end of a handle 70 (described further below). A portion of the electrical conducting pathway, for example, the portion at coronal end 62, is electrically coupled via a cable to an EAL device that measures, for example, the electrical resistance, impedance, or capacitance to detect physiologic apex 16 of root canal 12. For example, the EAL device can measure the ratio change between capacitance and impedance as obturation core 58 approaches physiologic apex 16 of root canal 12 to detect when, for example, apical end 60 of obturation core 58 is at physiologic apex 16 of root canal 12. For example, capacitance increases significantly near physiologic apex 16 of root canal 12, while impedance decreases significantly near physiologic apex 16 of root canal 12. The ratio change in capacitance and impedance can be outputted as an audio signal (e.g., periodic tone) to indicate when obturation core 58 nears physiologic apex 16 of root canal 12. In such embodiments, obturation core 58 and the EAL device can be used to ensure obturation core 58 is fully inserted in root canal 12, instead of or in addition to using tomographic and planar images generated by, for example, computed tomography (CT) such as cone-beam computed tomography (CBCT), intraoral radiographic imaging, magnetic resonance imaging, or ultrasonic imaging.

In some embodiments, the electrical conducting pathway is formed by either an internal or external wire extending from apical end 60 to coronal end 62. For example, the wire can be centered throughout obturation core 58, or the wire can be disposed on the exterior surface of obturation core 58. In some embodiments, the entire obturation core 58 is made of an electrically conductive material such that the entire obturation core 58 forms the electrical conducting pathway. In some embodiments, the electrically conductive material can be a metal or metal alloy, for example, gold, silver, platinum, aluminum, copper, titanium, titanium gold, nickel-titanium, titanium nitride, indium tin oxide, tin oxide, palladium, and stainless steel. In some embodiments, the electrically conductive material can be a conductive polymer, for example, polyaniline, polypyrrole, doped polyacetylene, polythiophenes, polyazulene, polyfuran, polyisoprene, and any other suitable conductive plastics.

Figure 17:
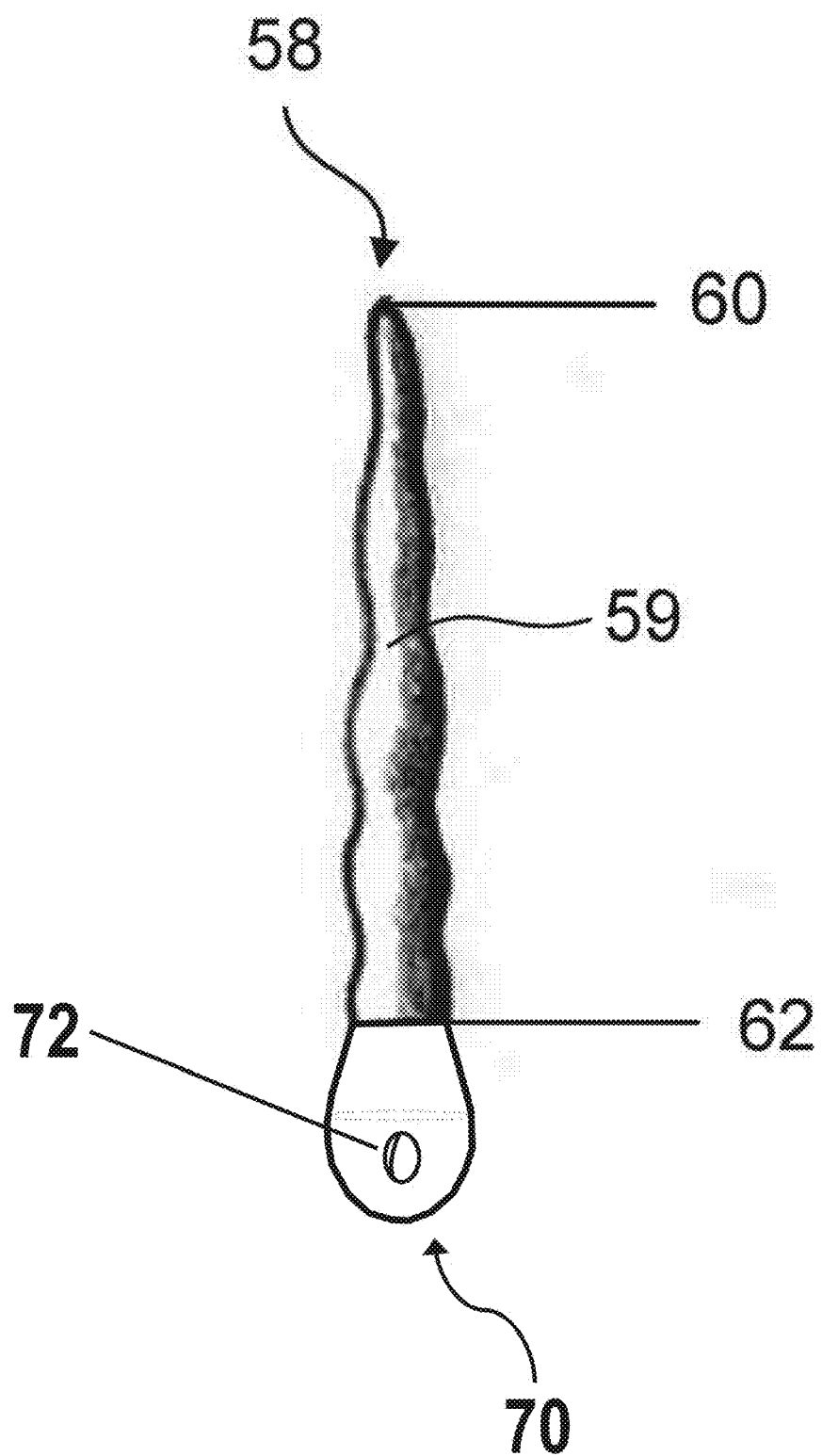
FIG. 17 illustrates a customized obturation core with a handle and interface, according to an embodiment.

In some embodiments, obturation core 58 can also include a handle 70 configured to allow a dentist to manipulate obturation core 58, for example, to allow the dentist to easily move obturation core 58 relative to root canal 12. FIG. 17 illustrates an exemplary obturation core 58 with handle 70 according to an embodiment. Handle 70 can be formed at coronal end 62 of obturation core 58. Handle 70 can have any suitable shape that a dentist can grip using, for example, fingers or an instrument configured to engage handle 70, thereby allowing the dentist to insert, adjust, or remove obturation core 58 relative to root canal 12. In some embodiments, handle 70 can have an elongated disc shape (as shown in FIG. 17), a prolate spheroid, a three-dimensional polygonal shape (e.g., post, prism, box, cuboid, orthotope, etc.), spheroid shape (e.g., oblate, prolate, etc.), ovoid shape, cylindrical shape, a conical shape, or any other suitable shape. During use, the dentist can grip handle 70 with the dentist's fingers or with an instrument configured to engage handle 70, and then insert, adjust, or remove obturation core 58 in root canal 12 by manipulating handle 70.

In some embodiments, handle 70 can include an interface 72 that is configured to cooperatively engage with a tool, for example, a probe with a hook, explorer, carver, pliers, wire, excavator, or forceps. In some embodiments, interface 72 can be, for example, a circular through hole, positioned above an axial centerline of handle 70. Such a circular through hole interface 72 can be configured to receive a correspondingly shaped protrusion (e.g., a hook or prong) of the tool. In other embodiments, interface 72 can be a recess, protrusion (e.g., a post or hook), or groove formed in handle 70 configured to cooperatively engage with a removal tool. During use, the dentist can engage interface 72 with the tool and then insert, adjust, or remove obturation core 58 in root canal 12 by manipulating the tool.

Figure 18:
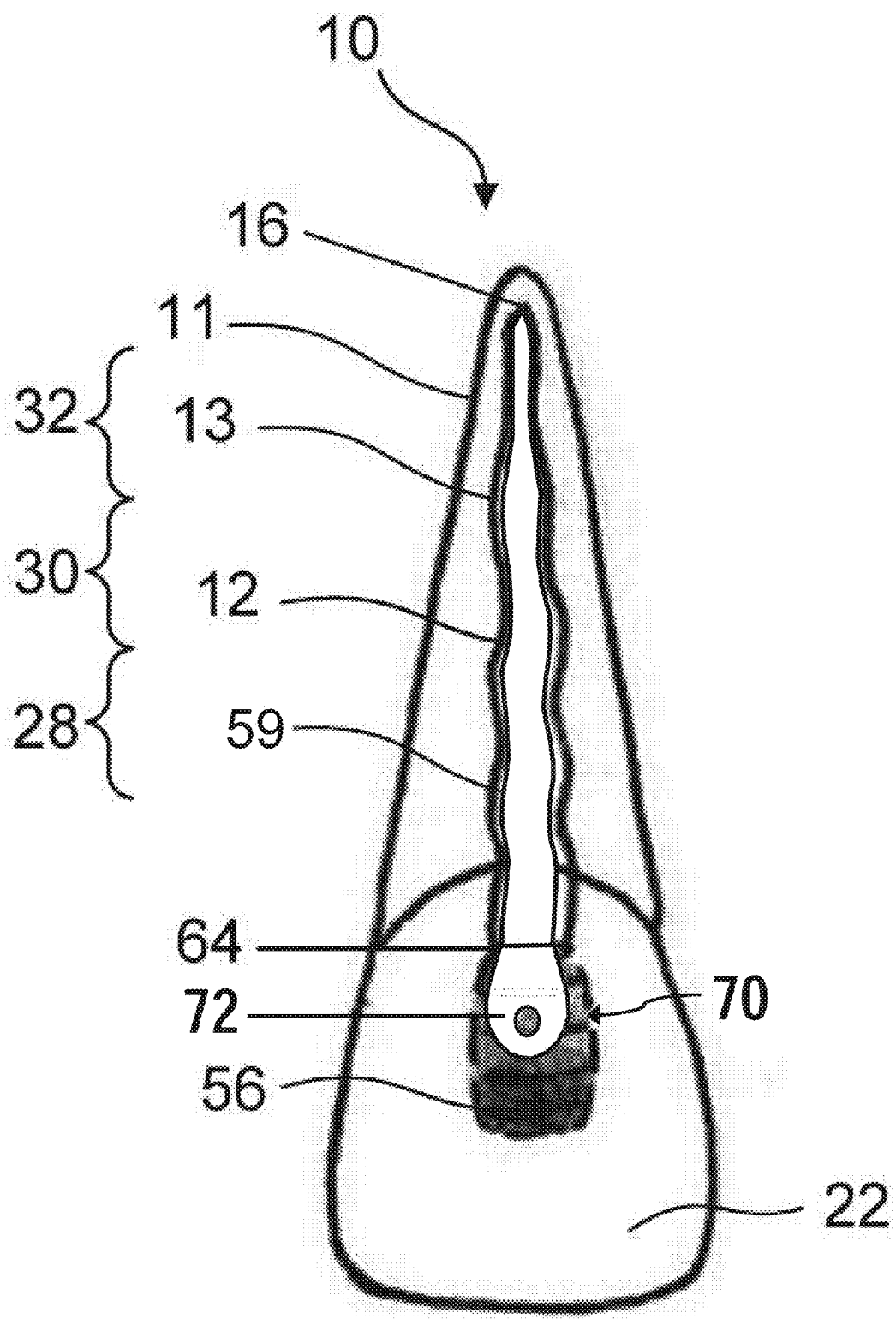
FIG. 18 illustrates a lingual view of a human anterior tooth after irrigation and cleaning and after insertion of a customized obturation core with a handle and interface, according to an embodiment.

FIG. 18 illustrates a lingual view of human anterior tooth 10 with an exemplary obturation core 58 with handle 70 inserted within root canal 12. A dentist can remove or adjust obturation core 58 within root canal 12 by manipulating handle 70, for example, by engaging interface 72 with the tool and then manipulating the tool. After obturation core 72 is positioned correctly in root canal 12, either handle 70 can be removed from coronal end 62 of obturation core 58, for example, by cutting handle 70 off using a rotary drill or other tool, or handle 70 can simply be covered by filling material that fills access opening 56 of tooth 10. In some embodiments in which handle 70 is not removed, handle 70 can define a smooth surface or be made of a material that does not bond to a sealant or filling material so that obturation core 58 can be more easily removed from root canal 12. In some embodiments, obturation core 58 and handle 70 can be sized such that handle 70 is positioned below orifice 64 of root canal 12.

While various embodiments of the present invention have been described above, it should be understood that they have been presented by way of example, and not limitation. It will be apparent to persons skilled in the relevant art that various changes in form and detail can be made therein without departing from the spirit and scope of the invention.

The present invention has been described above with the aid of functional building blocks and method steps illustrating the performance of specified functions and relationships thereof. The boundaries of these functional building blocks and method steps have been arbitrarily defined herein for the convenience of the description. Alternate boundaries can be defined so long as the specified functions and relationships thereof are appropriately performed. Any such alternate boundaries are thus within the scope and spirit of the claimed invention. One skilled in the art will recognize that these functional building blocks can be implemented by discrete components, application specific integrated circuits, processors executing appropriate software and the like or any combination thereof. Thus, the breadth and scope of the present invention should not be limited by any of the above-described exemplary embodiments, but should be defined only in accordance with the following claims and their equivalents.

What is claimed is:

1. A customized core for obturating a root canal defining a non-uniform contoured volume that includes an apical portion including a physiologic apex of the root canal, the customized core comprising:
   a pre-formed body shaped to match at least the apical portion of the non-uniform contoured volume such that, when the pre-formed body is inserted in the root canal, the pre-formed body substantially fills the apical portion including the physiologic apex, thereby forming a seal substantially impervious to bacteria and tissue fluid in the apical portion including the physiologic apex,
   wherein the pre-formed body is generated by a computer controlled manufacturing system based on a three-dimensional image of the root canal,
   wherein the pre-formed body further comprises a handle formed at a coronal end of the pre-formed body, and configured to allow a user to manipulate the pre-formed single-piece body relative to the root canal, and
   wherein an exterior surface of the pre-formed single-piece body comprises a biocompatible and bioactive material comprising calcium silicate.

2. A customized core for obturating a root canal having an apical portion, a middle portion, and a coronal portion, the customized core comprising:
   a pre-formed single-piece body shaped to match a contour of the root canal such that, when the pre-formed single-piece body is inserted in the root canal, the pre-formed single-piece body substantially fills the apical portion, the middle portion, and the coronal portion of the root canal, thereby forming a seal substantially impervious to bacteria and tissue fluid in the root canal,
   wherein the pre-formed single-piece body comprises a material that expands when exposed to a catalyst and remains dimensionally stable.

3. The customized core of claim 2, wherein the pre-formed single-piece body comprises a biocompatible and bioactive material.

4. A customized core for obturating a root canal having an apical portion, a middle portion, and a coronal portion, the apical portion including a physiologic apex of the root canal, the customized core comprising:
   a pre-formed single-piece body shaped to match a contour of the root canal such that, when the pre-formed single-piece body is inserted in the root canal, the pre-formed single-piece body substantially fills the apical portion including the physiologic apex of the root canal, thereby forming a seal substantially impervious to bacteria and tissue fluid in the apical portion including the physiologic apex of the root canal,
   wherein the pre-formed single-piece body is generated by a computer controlled manufacturing system based on a three-dimensional image of the root canal.

5. The customized core of claim 4, wherein the pre-formed single-piece body further comprises a handle formed at a coronal end of the pre-formed single-piece body, and configured to allow a user to manipulate the pre-formed single-piece body relative to the root canal.

6. The customized core of claim 4, wherein the root canal defines a non-uniform contoured volume.

7. The customized core of claim 4, wherein the pre-formed single-piece body comprises a biocompatible and dimensionally stable material.

8. The customized core of claim 4, wherein the pre-formed single-piece body comprises an antimicrobial material.

9. The customized core of claim 4, wherein the pre-formed single-piece body comprises a material that is substantially impervious to bacterial and tissue fluid infiltration.

10. The customized core of claim 4, wherein the pre-formed single-piece body comprises a radiopaque material.

11. The customized core of claim 4, wherein the pre-formed single-piece body comprises a material that expands when exposed to a catalyst and remains dimensionally stable.

12. The customized core of claim 11, wherein an expansion ratio of the material varies along a length of the pre-formed single-piece body.

13. The customized core of claim 4, wherein at least a portion of the pre-formed single-piece body is a non-dentin color.

14. The customized core of claim 5, wherein the handle is configured to be:
   removed from the coronal end after the pre-formed single-piece body is positioned in the root canal; or
   covered by a filling material after the pre-formed single-piece body is positioned in the root canal.

15. The customized core of claim 5, wherein the handle comprises an interface configured to cooperatively engage with a removal tool configured to remove the pre-formed single-piece body from the root canal.

16. The customized core of claim 4, wherein an exterior surface of the pre-formed single-piece body is smooth such that the exterior surface does not bond to a sealant between the pre-formed single-piece body and the root canal.

17. The customized core of claim 16, wherein the exterior surface of the pre-formed single-piece body is hydrophobic.

18. The customized core of claim 16, wherein the exterior surface of the pre-formed single-piece body has a coefficient of friction within a range of about 0.0 to about 0.15.

19. The customized core of claim 16, wherein the exterior surface of the pre-formed single-piece body comprises polytetrafluoroethylene (PTFE).

20. The customized core of claim 4, wherein an exterior surface of the pre-formed single-piece body is rough such that the exterior surface creates a mechanical interlock with any sealant in the root canal.

21. The customized core of claim 4, wherein the pre-formed single-piece body comprises a material that dissolves when exposed to a solvent.

22. The customized core of claim 4, wherein a density of the pre-formed single-piece body varies along a width of the pre-formed single-piece body.

23. The customized core of claim 4, wherein the pre-formed single-piece body defines a conductive pathway from an apical end to a coronal end of the pre-formed single-piece body.

24. The customized core of claim 4,
wherein an exterior surface of the pre-formed single-piece body comprises a biocompatible and bioactive material comprising calcium silicate.

25. The customized core of claim 4, wherein the computer controlled manufacturing system comprises a computer numerically controlled machine.

26. The customized core of claim 4, wherein the computer controlled manufacturing system includes an additive manufacturing machine.

* * * * *